United States Patent [19]

Isenberg

[11] 4,428,817
[45] Jan. 31, 1984

[54] SENSOR CELL STRUCTURE FOR OXYGEN-COMBUSTIBLES GAS MIXTURE SENSOR

[75] Inventor: Arnold O. Isenberg, Pittsburgh, Pa.

[73] Assignee: Westinghouse Electric Corp., Pittsburgh, Pa.

[21] Appl. No.: 407,675

[22] Filed: Aug. 12, 1982

[51] Int. Cl.³ .......................................... G01N 27/58
[52] U.S. Cl. ................................... 204/412; 204/427
[58] Field of Search ............... 204/412, 427, 428, 429, 204/1 S; 422/94, 95, 96, 97; 324/425

[56] References Cited

U.S. PATENT DOCUMENTS

| | | | |
|---|---|---|---|
| Re. 28,792 | 4/1976 | Ruka et al. | 204/1 T |
| 4,040,929 | 8/1977 | Bauer et al. | 204/426 |
| 4,145,272 | 3/1979 | Nakamura et al. | 204/412 |
| 4,233,142 | 11/1980 | Rohr et al. | 204/429 |
| 4,264,425 | 4/1981 | Kimura et al. | 204/412 |
| 4,285,790 | 8/1981 | Isenberg et al. | 204/195 R |

Primary Examiner—G. L. Kaplan
Attorney, Agent, or Firm—T. R. Trempus

[57] ABSTRACT

A thin film solid electrolyte cell structure for use as a gross-oxygen combustibles sensor that measures combustibles and oxygen in the presence of each other, generates two currents, one proportional to the amount of combustibles, the other proportional to the amount of oxygen. An electrode is sealed to a porous mechanical support member by a thin film solid electrolyte which also seals the support member. The sealed support member divides a sensor apparatus into two zones, one of which contains an oxygen containing reference gas, the other of which contains the gas to be measured.

6 Claims, 2 Drawing Figures

SENSOR CELL STRUCTURE FOR OXYGEN-COMBUSTIBLES GAS MIXTURE SENSOR

BACKGROUND OF THE INVENTION

1. Field of the Invention

The invention is directed to a sensor cell structure for a gross-oxygen-gross-combustibles sensor for the measurement of combustibles and oxygen in the presence of each other.

2. Description of the Prior Art

Solid state oxygen sensors and combustion sensors consisting of an electrochemical cell which utilizes an oxygen-ion conducting solid electrolyte are known in the art. These sensors operate in two basic modes, one of which is based on a potential measurement while the other is based on a current measurement.

In the potential measurement type of sensor, oxygen activity in an unknown environment is compared to oxygen activity in a known environment according to the Nernst-relationship. The presence of fuel determines the oxygen activity at high temperatures. Therefore, one can, when conditions are correctly chosen, determine the combustibles content of a gas through oxygen activities measurements. However, a low oxygen activity in an inert gas can produce a voltage signal indicating the presence of combustibles when no combustibles are actually present. As a result of this phenomenon, potential measurements require that the gas composition be approximately known to draw conclusions concerning the combustibles content thereof.

The sensor can also function in a current measuring mode which analyzes the oxygen concentration by measuring the current which can be supported by the electrochemically active gas species. In the instance of excess oxygen, oxygen ions are transported through a solid oxide electrolyte from a first electrode to a second electrode. If the access of oxygen is restricted to the electrode from which oxygen enters the electrolyte as an ion, the current becomes indicative of the oxygen ions that are allowed to travel between the electrodes. The current detecting sensor is not an absolute measuring device and must be calibrated with known gas mixtures. The current measuring mode is generally used to analyze gas at a temperature above 800° C. by using a stabilized zirconia electrolyte.

In the presence of excess fuel, most or all oxygen is eliminated at the temperatures at which a current mode sensor is useful because of chemical reaction with the fuel. The electrode which is in contact with combustibles is at a very low oxygen activity while the other electrode is maintained at a high oxygen activity through contact with an oxygen reference, such as air. The cell produces a voltage according to the Nernst-relationship which can drive a current caused by oxygen ion flow in the direction of the lower oxygen activity side. Such a cell operates in a fuel cell mode. Through the restriction of the access of combustibles to the low oxygen side, and through calibration, the current mode can be advantageously utilized to measure excess fuel. At present, the current mode requires higher temperatures than the voltage mode, because of the reduced electrolyte resistance required to enable the development of an adequate current which is limited by the access of combustibles to one electrode.

It is an object of this invention to provide a sensor cell structure which usefully employs the current measurement mode at much reduced temperatures even below 500° C.

It is an additional object of this invention to provide a thin film electrolyte, solid state sensor cell structure which can measure oxygen and combustibles in the presence of each other at such low temperatures that the gases will not react with each other.

It is also an object of this invention to provide a solid state sensor cell mounted on a porous substrate, whereby the sensor cell electrolyte is a thin film layer which effectively seals the porous substrate.

SUMMARY OF THE INVENTION

A thin film solid electrolyte sensor for the low temperature measurement of oxygen and combustibles in the presence of each other includes a porous support member on which is supported two sensor cell structures. One cell structure functions as an oxygen sensor while the other cell structure functions as a combustibles sensor. The oxygen sensor cell includes a pair of electrodes with a thin film layer of solid electrolyte disposed therebetween. The solid electrolyte is between about 5 to 100 $\mu$m in thickness and seals one of the electrodes to the porous support. An electrode connection layer made of an electronically conductive material which does not permit the diffusion of any gaseous species, provides electrical contact with the electrode sealed to the support by the electrolyte. The other electrode is a non-catalytic material in which combustibles and free oxygen will not combine spontaneously when in contact therewith. The combustibles sensor cell structure is similar to that of the aforedescribed oxygen sensor with the exception that a catalytic electrode is substituted for the non-catalytic electrode. The solid electrolyte is preferably a single entity sealing one electrode of each cell against the porous support except in areas of electronic contact. The other side of the porous support is in communication with an isolated air reference supply. Each sensor cell can be in communication with means to detect and measure both current and potential differences proportional to the amount of oxygen and combustibles in the gross-oxygen-gross-combustibles mixture contacting the sensor cells.

BRIEF DESCRIPTION OF THE DRAWING

The above, as well as other features and advantages of this invention will become apparent through consideration of the detailed description in connection with the accompanying drawings in which.

DESCRIPTION OF THE PREFERRED EMBODIMENT

Figure 1:
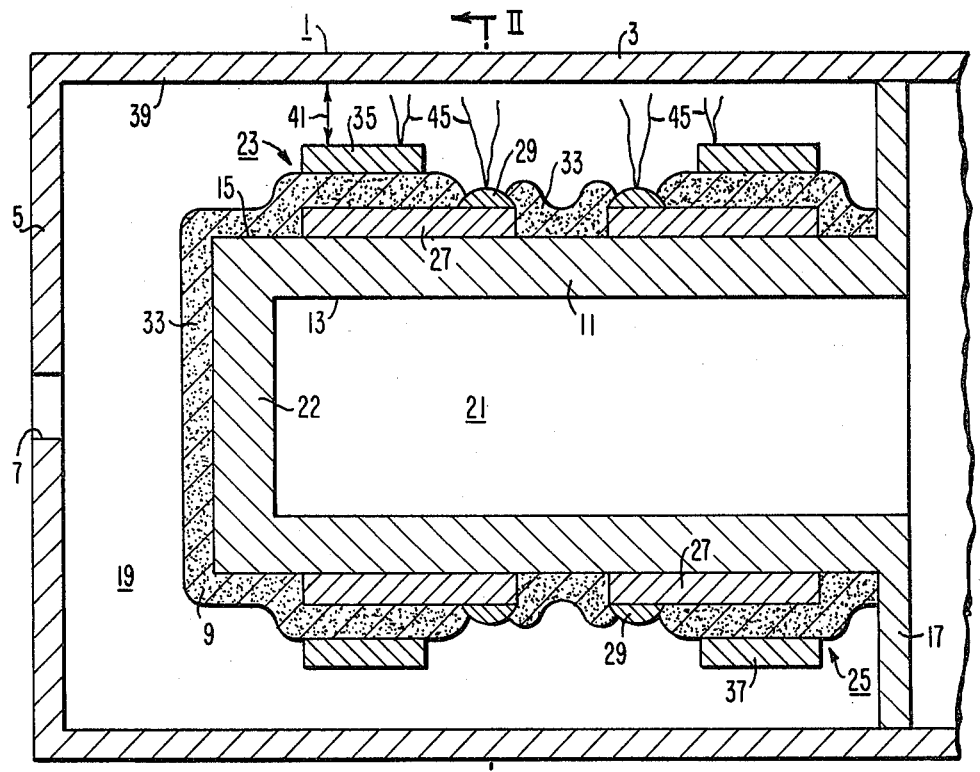
FIG. 1 is a sectional, pictorial illustration of a sensor cell structure according to the invention.
Figure 2:
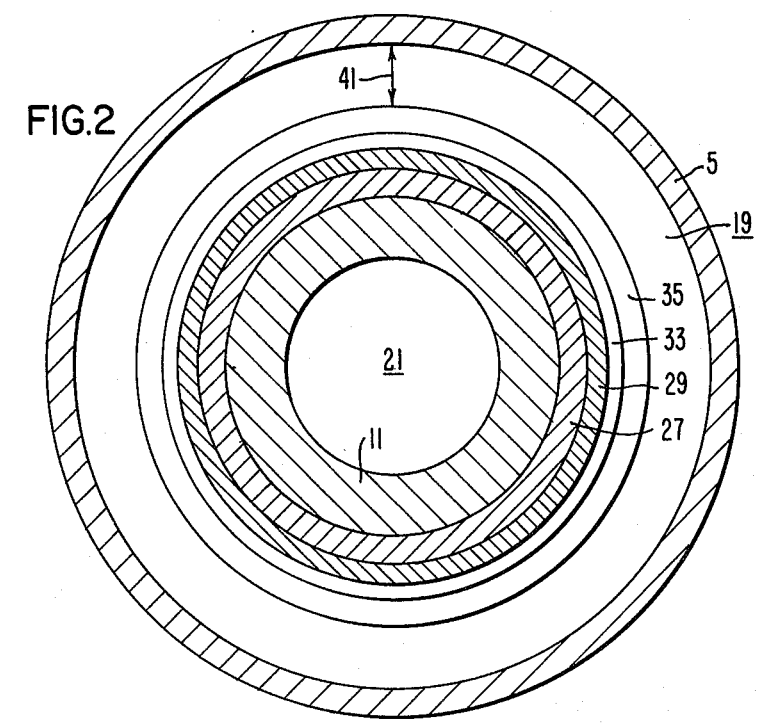
FIG. 2 is a section through FIG. 1 along lines II—II.

The gas sensor apparatus of this invention is generally indicated by the reference character 1 and includes an outer tubular housing 3 with an end plate 5 having an aperture 7 therein. A tubular electrochemical sensor generally indicated by the reference character 9 is enclosed and sealed within the housing 3. The sensor 9 includes a porous supporting member 11 having an inner surface 13 and an outer surface 15. The supporting member 11 is mounted within the housing 3 by a radially extending shoulder portion 17 and together therewith defines within the sensor 1, two zones 19 and 21. The specific technique utilized to mount a sensor supporting member within a sensor housing as well as physical configuration of the sensor can vary. As will become evident, the important consideration in the construction of a sensor cell according to this invention is the isolation of zone 21 from zone 19 by means of a solid electrolyte deposited on a porous support. Returning to the illustrated electrochemical sensor cell 9, the porous, cell supporting member 11 is concentrically mounted within the housing 3 with an end portion 22 proximate the aperture 7. The outer tubular housing 3 is itself in communication with additional support structure and equipment which are well known in the art and not illustrated herein.

The electrochemical sensor 9 consists of a first cell 23 and a second cell 25 circumferentially disposed on the outer surface 15 of the porous, tubular member 11 which functions as a mechanical support for this solid state sensor. The first cell 23 is an oxygen extraction cell which measures oxygen and the second cell 25 is a combustibles detection cell. Because the physical structure of the two sensor cells is similar, their components will be described jointly with distinctions indicated where necessary. Each cell has a coated electrode band 27 and an electrode connection layer 29, on top of the electrode band 27. The electrode connection layer 29 can consist of a ring-like continuous member in contact with band 27 as shown, or a single-spot like, electrically conductive member. The electrode connection layer 29 is made of an electronically conductive material which does not allow diffusion of gaseous species, especially hydrogen. Preferably this layer 29 consists of doped lanthanum chromite and functions as a contact point for the circuitry of each cell. A thin film layer of electrolyte 33 of between about 5 to 100 $\mu$m in thickness, preferably 10 to 50 $\mu$m is applied over the electrodes 27 of both cells, sealing the electrodes against the porous support 11 and also sealing the exposed portions of the porous support tube as at end portion 19. The thin film electrolyte 33 is preferably yttria doped zirconia, but can also be doped with other elements such as calcia or rare earth elements to render it conductive. A non-catalytic electrode 35 is applied to the electrolyte 33 of cell 33 so as not to promote the reaction of oxygen with combustible prior to the diffusion of the combustibles to cell 25. The non-catalytic electrode 35 can consist of silver, gold, poisoned platinum group metals or oxides, such as rare earth chromites doped or undoped, doped indium oxide, doped titania, rare earth manganites, or cobaltides or nickellates dopes or undoped, alone or in mixtures. A catalytic electrode 37 is applied to the electrolyte 33 of cell 25. The catalytic electrode 37 lowers the activation energy barrier, thus facilitating the reaction of the combustibles contacting the cell 25 at low temperatures. While the catalytic electrode 37 is preferably made of a platinum-group metal, it can also, for example, consist of a porous gold or silver electrode containing activating compounds such as perovskite-type oxides, platinum group metals, praseodymium oxide, or cobalt praseodymium oxide.

The electrodes 35 and 37 are also in the form of a band as is the case with the electrodes 27. The electrolyte 33 and the electrode connection layers 29 cooperate to effectively seal the porous support member and electrodes 27. While the electrolyte 33 is illustrated as overlapping the electrode bands 29 to form a seal, it is also possible to employ an electrode band configured to overlap the electrolytes.

The structure of the cell housing 3 has a relatively narrow gap width between the inside surface 39 of the housing 3 and the sensor cell 23 as indicated by the arrow 41. This gap 41 can be as small as 25 $\mu$m so that the oxygen in the gases being measured is completely extracted through contact with cell 23 prior to the diffusion of the combustibles to cell 25. Additionally, the porous support member 11 should have a thermal expansion coefficient compatible with the electrolyte 33 and the cell housing 3 to minimize thermally induced structural damage.

The gross-oxygen-gross-combustibles atmosphere to be examined with this sensor, enters the housing 3 through aperture 7 into the first zone 19 and contacts sensor cell 23 where the oxygen is extracted from the gross mixture electrochemically and transported to the second zone 21. Although the tubular portion 13 of the support member 11 is porous as discussed above, the electrolyte 33 seals the outer surface 17 thereof against uncontrolled diffusion. The combustibles, now substantially void of oxygen, diffuse to cell 25 and are electrochemically oxidized.

The operation of oxygen ion conductive cells is well known in the art and is described and illustrated in U.S. Pat. No. Re. 28,792. Additionally, a molten carbonate electrolyte cell, which is similar in function to the sensor described herein is shown in U.S. Pat. No. 4,285,790. Both of these patents are assigned to the assignee of the present invention and are incorporated herein by reference.

Both the oxygen sensor cell 23 and the combustibles sensor cell 25 can be provided with multiple leads 45 from electrodes 27 and 35, and 28 and 37 respectively, in communication with current detection means and means to measure the potential difference between the electrodes of each cell.

The utilization of a thin film electrolyte of between about 5 to 100 $\mu$m thick allows the construction of a device which can operate at relatively low temperatures because of reduced sensor cell resistance. As a result, the solid state, integrated sensor of this invention can potentially be used to measure either oxygen alone at a temperature of about 300° C. or higher by means of the oxygen sensor 23, combustibles such as diluted hydrogen, carbon monoxide and methane alone at a temperature of about 300° C. or higher through the combustibles sensor 25 or a gross oxygen-combustibles mixture at temperatures as low as between about 500° to 700° C. External or internal heating of the sensor can be utilized with the present solid state sensor design. For internal heating, a heater means can be mounted in the cavity defined by zone 21.

What is claimed is:

1. A cell structure for an oxygen-combustible gas sensor comprising:

a sensor housing;

a porous mechanical support member of electrically non-conductive material mounted in said housing and dividing said housing into a first zone in communication with a gas to be measured and a second zone in communication with an oxygen containing gas;

an oxygen sensor cell including a first electrode disposed on said porous member; an electrode connection layer in electrical contact with and providing a terminal for said first electrode, said electrode connection layer consisting of an electrically conductive material which does not allow gaseous diffusion therethrough; a thin film layer of solid electrolyte, a portion thereof contacting said electrode connection layer and overlapping said first electrode such that said solid electrolyte in combination with said electrode connection layer seals said first electrode onto said porous member, and a non-catalytic second electrode disposed on said solid electrolyte opposite said first electrode; and a combustibles sensor cell including a first electrode disposed on said porous member, an electrical connection layer in electrical contact with and providing a terminal for said first electrode, said electrode connection layer consisting of an electrically conductive material which does not allow gaseous diffusion therethrough, a further portion of said thin film of solid electrolyte contacting said combustibles sensor electrode connection layer and overlapping said combustibles sensor first electrode such that said solid electrolyte in combination with said combustibles sensor electrode connection layer seals said combustibles sensor first electrode onto said porous member, and a catalytic second electrode disposed on said solid electrolyte opposite said first electrode; said solid electrolyte and both said electrode connecting layers effectively seal said porous mechanical support member substantially isolating said first zone from said second zone;

whereby both said first electrode of said oxygen sensor cell and said first electrode of said combustibles sensor cell are in communications with the reference gas through said porous support while said non-catalytic second electrode of said oxygen sensor cell and said other catalytic second electrode of said combustibles sensor cell are in communication with the gas to be measured.

2. The cell structure of claim 1 wherein the thin film layer of solid electrolyte is between about 5 to 100 $\mu$m in thickness.

3. The cell structure of claim 2 wherein the thin film layer is between 10 to 50 $\mu$m in thickness.

4. The cell structure of claim 1 wherein the solid electrolyte thin film contacting the electrode connection layers of both sensor cells is partially overlapping said connection layers.

5. The cell structure of claim 1 wherein the non-catalytic electrode consists of a material selected from the group consisting of silver, gold, poisoned platinum group metals, doped rare earth chromites, doped indium oxide, doped titania and rare earth-chromites, manganites, cobaltides and nickellates; and the catalytic electrode consists of a material selected from the group consisting of platinum group metals, and porous gold or silver containing perovskite-type oxide impregnations.

6. The cell structure of claim 1 wherein the sensor housing is a tubular member, and wherein the porous mechanical support member includes a tubular portion having an outer surface, concentrically mounted within said tubular member in a spaced relationship and means to support said tubular portion therein and wherein the oxygen sensor cell and the combustibles sensor cell are disposed about the outer surface of said tubular portion.

* * * * *